United States Patent [19]

Törnblom

[11] Patent Number: 5,111,412
[45] Date of Patent: May 5, 1992

[54] COMPOSITE SENSING TRANSDUCER

[75] Inventor: Bengt H. Törnblom, Västerås, Sweden

[73] Assignee: Tornbloms Kvalitetskontroll AB, Västerås, Sweden

[21] Appl. No.: 434,504

[22] Filed: Nov. 9, 1989

Related U.S. Application Data

[63] Continuation of Ser. No. 152,545, Feb. 5, 1988, abandoned.

[30] Foreign Application Priority Data

Feb. 9, 1987 [SE] Sweden .................. 8700472
Sep. 15, 1987 [SE] Sweden .................. 8703555

[51] Int. Cl.⁵ .................. G01N 27/90; G01N 27/82
[52] U.S. Cl. .................. 364/571.04; 364/571.07; 364/550; 324/238; 324/225; 324/202; 73/618
[58] Field of Search .......... 364/550, 571.01, 571.04, 364/571.07, 507; 324/225, 238, 202; 73/618

[56] References Cited

U.S. PATENT DOCUMENTS

| | | | |
|---|---|---|---|
| 3,784,805 | 1/1974 | Rolle | 367/11 |
| 3,789,833 | 2/1974 | Bom | 128/661.01 |
| 4,092,867 | 6/1978 | Matzuk | 73/609 |
| 4,555,664 | 11/1985 | David et al. | 324/225 |
| 4,556,846 | 12/1985 | D'Hondt | 324/225 |
| 4,646,013 | 2/1987 | Törnblom | 324/225 |
| 4,661,777 | 4/1987 | Törnblom | 324/225 |

OTHER PUBLICATIONS

"Handbook of Modern Electronics and Electrical Engineering", Ed: Charles Belove, Pb: John Wiley and Sons.

Primary Examiner—Parshotam S. Lall
Assistant Examiner—V. Trans
Attorney, Agent, or Firm—Watson, Cole Grindle & Watson

[57] ABSTRACT

A device for simulating a moving test object sensing transducer uses a plurality of individual transducers which are stationary relative to each other (for example eddy-current based surface transducers), and a selector unit. The individual transducers are, for example, mounted in a plane parallel to the surface of the test object to be sensed and scan the test object with respect to a characteristic, for example a crack. The resultant simulated transducer signal is signal processed by means of, for example, automatic compensation and vector transformation techniques. By automatically switching in the individual transducers in succession, for example in a continuously recurrent sequence, signals originating from different individual transducers completely or partially determine different time portions of a resultant signal, and a quantity or combination of quantities is tested and/or measured by means of the transducers which in turn can be identified as deriving from different physical regions of the surface being tested.

20 Claims, 6 Drawing Sheets

COMPOSITE SENSING TRANSDUCER

This application is a continuation of application Ser. No. 152,545, filed Feb. 5, 1988 now abandoned.

TECHNICAL FIELD

The present invention relates to a device for monitoring (e.g. testing and/or measuring) a test object with respect to at least one quantity, in the test object, which device comprises a plurality of transducers which are arranged so as to at least partially sense respective different regions of the test object. The device also includes at least one selector, for example an electronic switch, and at least one signal processing unit having a memory function.

DISCUSSION OF PRIOR ART

The conventional method of scanning larger surfaces in, for example, crack detection, comprises moving, for example rotating, a surface transducer (e.g. a coil) rapidly across the surface to be scanned. In connection with the testing of rolled wire it is known to use a surface transducer rotating rapidly around the wire. Because of the speed of advance of the rolled wire, which is often very high, short, longitudinal cracks, may arise between the scanned turns by the scanning coil around the wire.

SUMMARY OF THE INVENTION

The present invention aims to provide a solution to these problems and other problems associated therewith and is characterized in that signals, directly or indirectly originating from the individual transducers, are adapted to be used via the at least one selector in a certain order, for example in a recurrent, selected sequence, and in that information about the contemporary compensation requirement of each individual transducer is at least partially adapted to be stored in periodically updated memory means, for example condensers, and in that this information is at least partially adapted to be used for compensation of the signals from the individual transducers.

DEFINITIONS

A few definitions of terms used in the specification will now be given:

The term TEST OBJECT is intended to cover, for example, wire, rod, tubes, billets, sheets, ingots or a stream of molten material, which may be at any temperature.

The term QUANTITY is used herein to mean, for example, dimension, shape, change, oxide scale, surface defect, crack or other test object defect. The concept "quantity" may also include a combination of quantities.

The term TRANSDUCER is intended to cover, for example, both transducers, sensors and combinations of these, i.e. everything that the skilled person may include in the concept "transducer" for example an eddy-current based surface transducer coil.

The term TIME PORTION means any time interval, for example, the portion of time comprised by a time sequence ($T_s$), for example $T_1$ in FIG. 2.

Term PULSE means, for example, a signal of a certain duration.

The term LO means "lift-off".

In a preferred embodiment, the device simulates a moving transducer because, for example, signals from several fixed individual transducers each giving rise to a time portion of a resultant signal represent the simulated movement of the transducer. The combination of the different transducer signals, for example the sequence, can be varied, thus representing various movements of the simulated transducer, for example the simulated scanning pattern or path, to be obtained. The advantage of this, in addition to the fact that no mechanically movable parts are required, is that very high transducer velocities can be simulated, which, among other things, results in the advantage that very short cracks can be detected.

BRIEF DESCRIPTION OF THE DRAWINGS

The invention will now be further described, by way of example, with reference to the accompanying drawings, wherein.

DESCRIPTION OF PREFERRED EMBODIMENTS

Figure 1:
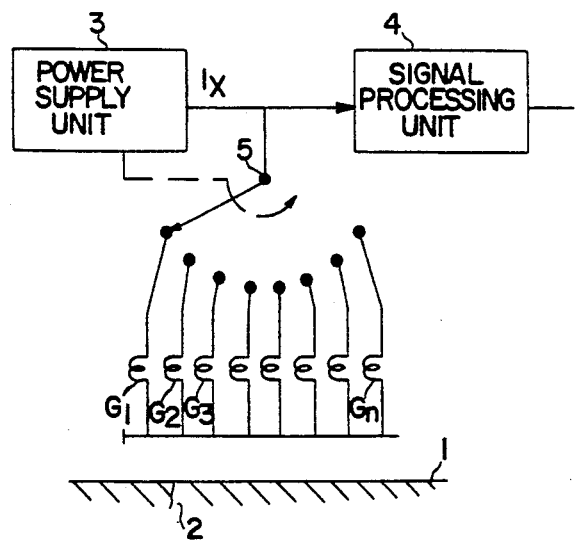
FIG. 1 shows, in schematic outline, the principle behind the invention.

FIG. 1 shows a number of transducers $G_1$ to $G_n$ positioned above different parts of a test object 1 which exhibits a crack 2. Via a selector 5 the transducers are switched in, one by one in succession, to a transducer power supply unit 3 (which supplies the transducer in question with a constant current $I_k$ of at least one carrier frequency and/or frequency component). The selector 5 steps continuously, and each step requires a time $T_1$ to $T_n$ the total time required for the completion of all steps being $T_s$ and called the sequence. The voltage across each transducer in turn is measured and processed in a common signal processing unit 4, the task of which is to detect the quantity being monitored, in this case the crack 2.

Figure 2:
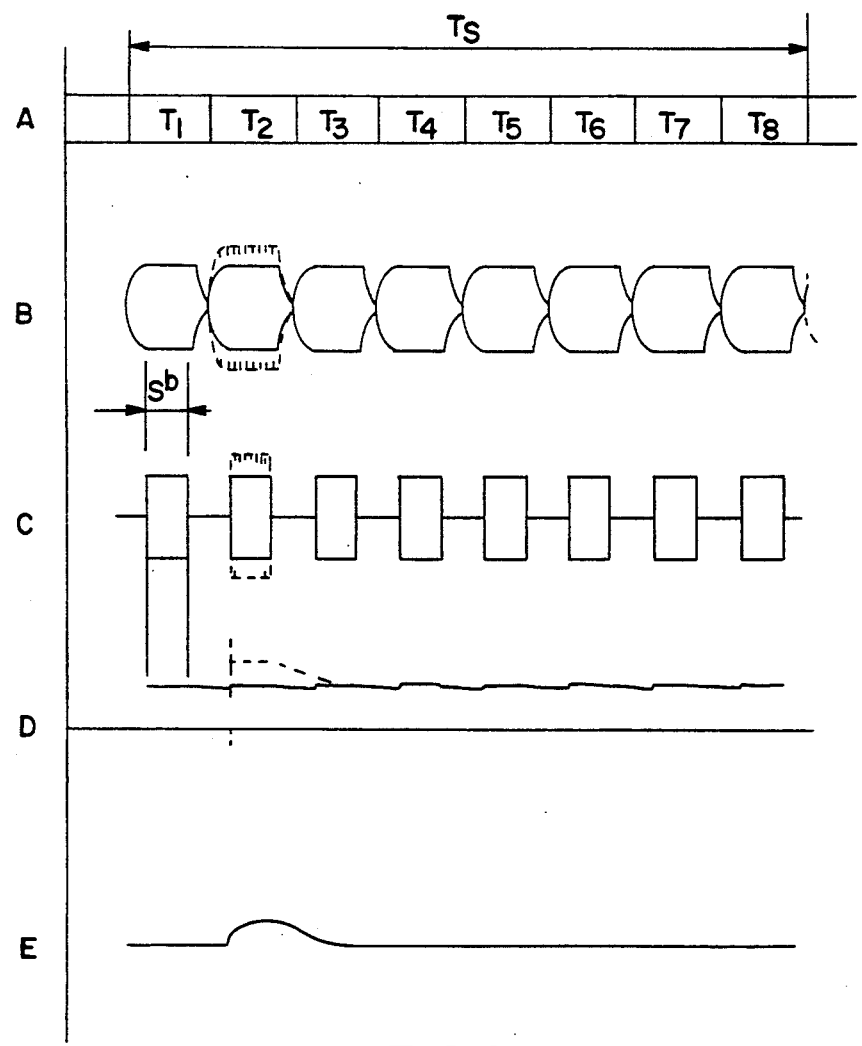
FIG. 2 shows graphs indicating how the device of FIG. 1 operates to sense the presence of a crack on a test object.

FIG. 2, shows in time sequence, events occurring with the apparatus of FIG. 1. Graph A in FIG. 2 shows the sequence $T_s$ along the time axis and the time $T_n$ that is allotted to each respective transducer (assumed to be eight in all) and which, for example, controls the stepping of the selector 5. When the selector assumes the first position, the voltage across transistor $G_1$ will increase at a rate determined by the current $I_k$, the impedance of the transducer $G_1$ and the inductive time constant of the transducer coil. In a corresponding manner, a decay transient is obtained when the selector 5 steps to the next transducer, in other words, when the current $I_k$ is interrupted at $G_1$, and these changes in voltage are shown in graph B in FIG. 2.

Graph B in FIG. 2 thus shows the input voltage to the signal processing unit 4, each following carrier frequency pulse train relating to the next transducer in the sequence of transducers $B_1$ to $G_n$.

Each transducer $G_1$ to $G_n$ is individually adjusted, for example balanced and compensated, so that the voltage drop across it is equal to a normal voltage level when, for example, the test object 1 is free of detectable defects. On the other hand, if a crack 2 is situated below one or more transducers (transducer $G_2$ in the illustrated example), the impedance of the transducer(s) will change so that the voltage across it/them will also change. This is shown by the dash-lined curves in graph B in FIG. 2.

In graph C of FIG. 2 the initial and final switching transients of the output pulses from the transducers have been gated away so as not to give rise to disturbance phenomena. Thus, only the central (Sb) amplitude-stable part of the output in graph B is included in graph C. The output from transducer $G_2$ in graph C also shows dash-lined regions caused by a detected crack.

Graph D in FIG. 2 shows a detected, for example rectified, signal derived from graph C. By utilizing a suitable discharge time constant in the rectifier, the signal acquires the appearance as shown in graph D and, where a possible crack is located below a transducer, the rectified signal deviates markedly from the normal level set by faultless regions of the test object 1.

Band E in FIG. 2 shows how by filtering, an accentuated "crack" signal can be derived from band D.

As will be readily realized, the transducers have to be electrically very similar to each other, for the base level in graph D of FIG. 2 to be acceptably smooth and stable when no detectable fault, i.e. in this case no crack, is present, since otherwise the "crack" signal could be concealed in background noise caused by individual differences between the transducer outputs. These differences in output can be caused by the selector 5. In the event that, for example, the signal in graph E of FIG. 2, despite measures taken to make the transducers similar to each other, does exhibit unacceptable noise, it may be advantageous to store the signal train of graph E during one or more sequences in a normal or reference case, and to use this stored signal directly or indirectly as a comparison signal when comparing with signals measured during testing at other times. The storing of signals from one sequence can take place with the aid of either analog or digital circuits, for example in an analog shift register or a computer.

If suitable, the transducers $G_1$ to $G_n$ may each be continuously connected to a respective transducer supply and the selector 5 only be used to select the input signal to be fed to the block 4. However, one significant advantage of the arrangement shown in FIG. 1 is that the same transducer supply unit 3 can be used for all the transducers. It should also be mentioned here that the selector 5 is desirably of electronic type, for example consisting of analog C/MOS switches controlled in conventional manner from, for example, crystal-controlled counters and the like.

To limit transient disturbances and the like upon switching from one transducer to another, the switching can be made, for example, via circuit components (e.g. resistances) selected in order to obtain a smoother switching sequence.

In connection with storing signal information, for example in a computer, possibilities are offered to change the order of the different transducer signals, so as to obtain several so-called resultant signals, representing different surface scanning patterns. Thus, the stored information from several transducers can be used to simulate several different transducer paths, in other words, a type of reorientation principle with possibilities for extensive use.

From FIGS. 1 and 2 it is clear that it is possible to decide from which time pulse the "crack" signal has been obtained and thus to decide which of the n transducers detected the defect. From this it follows that it is possible to precisely determine the location of the defect on the test object. Where more than one transducer is involved in defect detection both the position and the orientation/extension of the defect can be determined from a knowledge of the transducers involved in defect detection.

If correctly applied and performed, the invention comprises, in principle, all the advantages provided by a rotary surface transducer according to, for example, Swedish patent application No. 8503894-1.

Figure 3A:
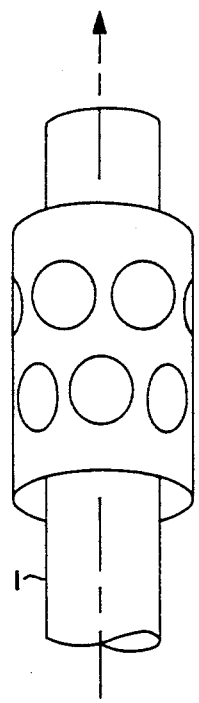
FIGS. 3 and 3a and 4 are examples of combination transducer arrangements within the scope of the invention.
Figure 3:
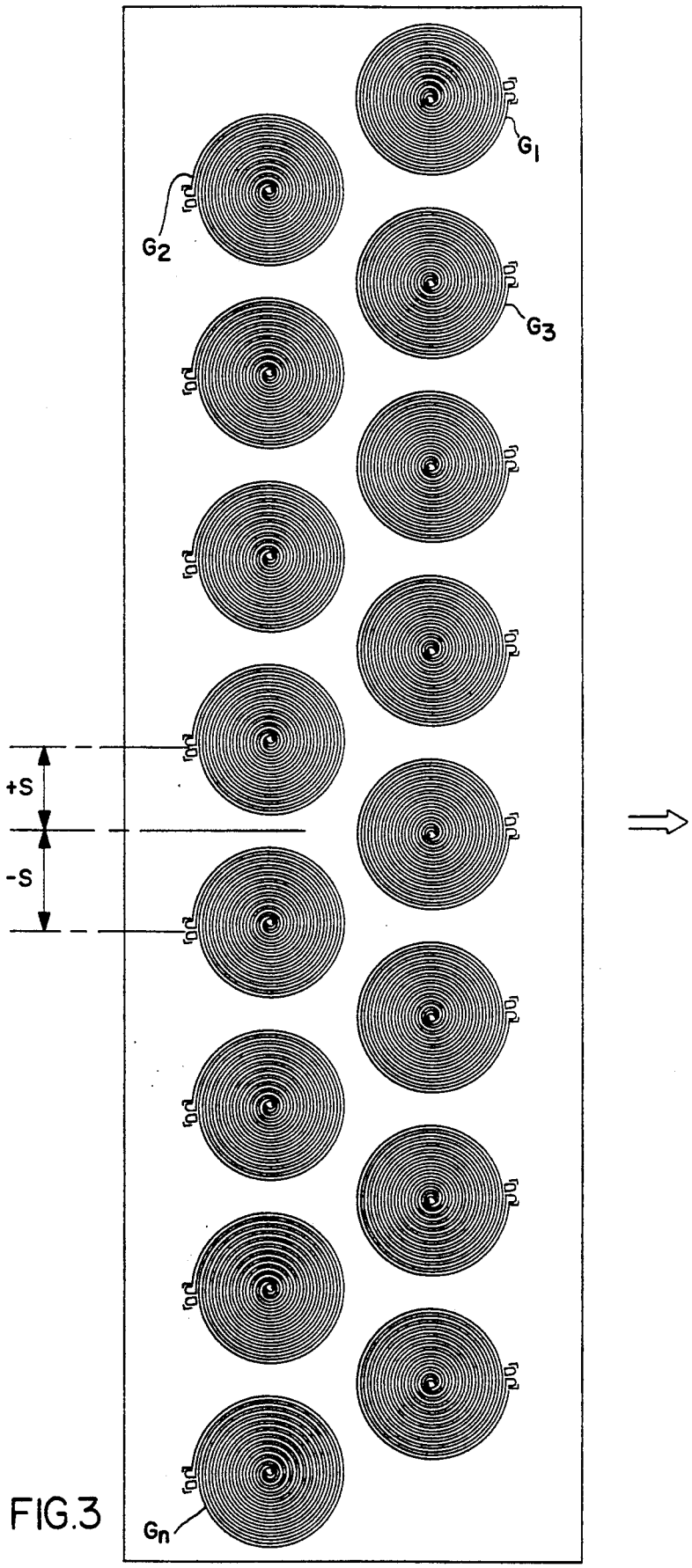
Figure 4:
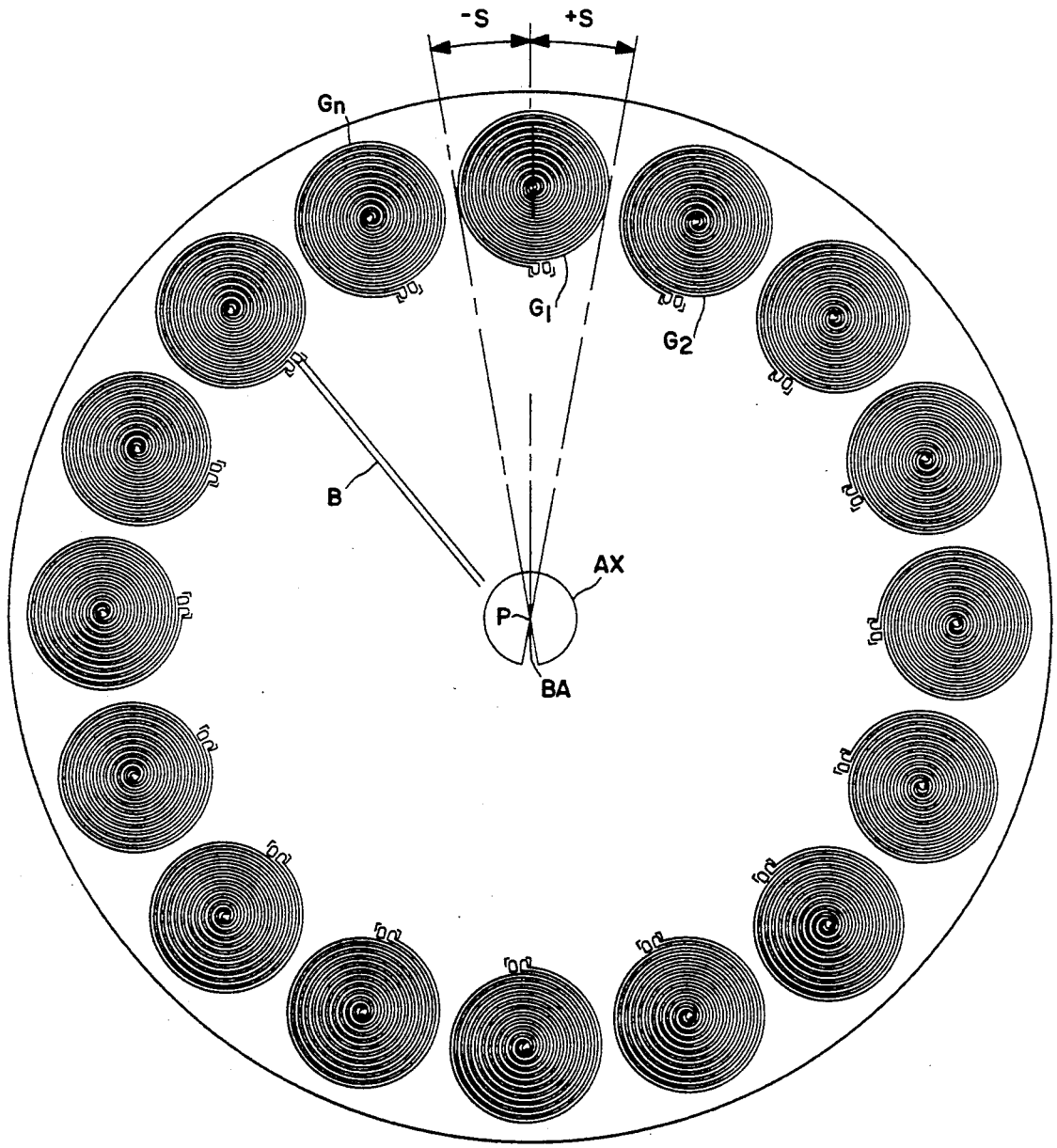

Concerning the transducers, the following can be said. FIG. 1 shows "n" transducers which together form a transducer arrangement. The transducer arrangement may have different appearances, for example as is shown in FIG. 3 or FIG. 4. For the invention to operate perfectly, the transducers should be as similar to each other as possible, both from a mechanical and an electrical point of view. For that reason the transducers in FIGS. 3 and 4 have been designed as coils of metallic foil, i.e. they have been etched out in a similar manner to that used for manufacturing conventional electronic printed circuit boards. Each surface transducer coil may be etched on one side of a laminated printed circuit card (chip), but, of course, it is also possible to etch a coil on each side so as to obtain double-sided transducers. In a double-sided design, the coils may be given winding directions so that their fields cooperate, whereby a series connection between the pair of coils on opposite sides of the board, can for example, take place by connecting the pair of coil windings via a centrally located through-lead. In FIGS. 3 and 4, which can each be considered to illustrate double-sided transducers, the connecting lugs coils $G_1$ and $G_n$ constitute the beginning and end of the series-connected coils. If it is desired to move one step further, several printed circuit board laminates can be stacked on top of each other and can be connected together in series (or in parallel), thus obtaining a multi-layer arrangement of transducer coils with a resultant higher inductance.

For several reasons it may be advantageous to place several transducers on one printed circuit board or other type of foil carrier. One reason for this economic but another reason may be that the transducers are likely to be almost identical with each other since the thickness and width of the foil can be expected to be the same for all the transducers printed on that board. FIG. 4 can be viewed as a printed circuit board comprising 16 surface transducers, for example intended for crack detection on a plane surface of a test object, the printed circuit board being placed in a plane parallel to the surface to be monitored. If suitable, of course, the printed circuit board can move relative to the surface of the object and, for example, can rotate around its own center. FIG. 3 may also consist of a printed circuit board but may comprise either a stiff printed circuit board or a flexible one. In the latter case, the printed circuit board can be bent around a rolled wire 1 (as shown in FIG. 3a) which moves in the direction of the arrows in FIGS. 3 and 3a. In this way, a transducer arrangement is obtained which surrounds the rolled wire, the entire surface of the rolled wire thus being scanned when this passes through the transducer arrangement. The arrangement illustrated in FIG. 3a can be seen as an annular transducer built up of surface transducers, in other words, a combination transducer.

If it is desired to increase the impedance of the transducer, for example because of limited inductance of a foil coil, each coil may, for example, be provided with a ferrite core, or a ferrite plate may, for example, be secured (e.g. glued) to that side of the printed circuit board which faces away from the test object.

The explanatory sketch of FIG. 3a shows how the flexible transducer arrangement surrounds the wire 1 and this arrangement may, for example, be placed in a metal tube and be cooled (e.g. with water) which, for example, forms a coolant filled space between the metal tube and the transducer arrangement.

To prevent, for example, longitudinal cracks on the rolled wire from passing undetected between adjacent transducer coils, these coils are desirably positioned, for example, in a zigzag pattern or the like, so that their field configurations overlap each other, viewed in the longitudinal direction of the rolled wire.

A transducer pattern according to FIG. 4 may, for example, be used on plane surfaces, such as on surfaces of test slabs. Also in this case it may be convenient to supplement the arrangement with an inner or an outer ring of transducers so as to obtain a zigzag pattern, or to fill the surface completely with transducers.

By etching out simple foil-type transducers, as described here, many interesting possibilities present themselves. It is also possible, for example, to apply the foil-type transducer to a flexible foil carrier which can be glued or otherwise adhered to the test object, for example at the corners and in other places which are difficult to reach. With this arrangement a type of "sticking plaster" is provided with transducers.

It is also possible to diffuse a metal layer onto a ceramic plate and then to etch out one or more foil coils directly on the plate. In this way it is possible, for example, to reduce the lift-off distance to the maximum extent in the case of the monitoring of hot test objects, especially if the ceramic plate is water-cooled on the foil side. In a corresponding manner the ceramic plate can be replaced by a ceramic tube, or the like, to permit the testing of elongate, for example round, test objects, through which tube the test object, for example the rolled wire, is allowed to pass. The ceramic tube is suitably cooled by water on the outside, for example via a water space specially provided.

In spite of the fact that care has been taken to make the transducers as identical to each other as possible (e.g. with the aid of etching techniques) they may, however, differ from each other to such an extent that it downgrades the measurement properties. For this reason it may be necessary to mount trimming components for individual balancing and compensation of the respective transducer coil. The trimming components may be mounted direct on the transducer laminate adjacent to the transducers and can be, for example, potentiometers and/or adjustable capacitors, mounted in parallel with or in series with the transducer coil. Since the transducer has a Q-value, it may also be necessary to adjust the amplification in the respective transducer branch so that the transducer signals in the reference case show the same signal amplitude. Each transducer can also have an individual possibility for vertical adjustment, so that the lift-off signal may be set as closely as possible at the same value for all the transducers.

Producing coils by etching is nothing new per se. However, the novelty resides in the manner in which the coils are used as described in this specification, i.e. utilizing the advantages obtained by the use of etched, multiple coils.

The transducer arrangement may advantageously be mounted to permit transverse motion relative to the test object, for example so that a limited oscillating movement or the like is imparted to the transducer arrangement. This reduces the requirement for the field configurations of the transducers to overlap one another at rest.

The transducer arrangement according to FIG. 4 may be stationarily or, for example, movably journalled via the axis AX at point P. If, in the latter case, the transducer arrangement is allowed to move/rotate back and forth, i.e. oscillate through the angle $\pm S$, the field configurations from the transducers will overlap each other well, whereby, for example, the scanned surface becomes more homogeneous in nature. As an alternative to different zigzag patterns, the transducer arrangement can be oscillated, which in certain applications is clearly more favorable. A consequence of this is that the transducers can be connected, for example via a simple cable of strips of metallic foil (B) at the center of the transducer arrangement, to the electronic unit 4 and to the transducer supply unit 3. Water for cooling, for example, may be connected at point P via a suitable hose and the like.

In the monitoring of round test objects, such as tubes and the like, the curved/tubular transducer arrangement shown in FIG. 3 is preferred and can be oscillated in a similar manner (e.g. through distances $+S$, $-S$), thus obtaining a very uniform magnetic field configuration which is especially well adapted to the detecting of long axial flaws, and the like defects.

The combination of a high simulated transducer velocity and a limited oscillation provides considerable advantages from the point of view of measuring technique compared with conventional mechanical solutions and arrangements.

The tubular transducer arrangement shown in FIG. 3 also enables measurement of, for example, the roundness of the rolled wire, the dimension in several directions, the position of cracks along the periphery of, for example, wire, etc. Other quantities may also be monitored because of the homogeneous and uniform field configuration.

As is well-known, the suppression of the lift-off dependence is an important feature in eddy current testing using surface transducers. Swedish patent application 7507857-6, British Patent 2041535, U.S. Pat. Nos. 4,646,013 and 4,661,777 and U.S. patent application Ser. Nos. 926,850 and 702,314 (both filed in the name of Törnblom on Nov. 3, 1986 and Feb. 15, 1985, respectively), for example describe different ways of coping with the LO problem.

In the case of eddy current testing, a device according to the present invention involves the same type of problems as those arising in the above-mentioned patents/applications, since in practice the transducer arrangement is almost always somewhat inclined relative to the surface of the test object. Therefore, the signal processing unit 4 in FIG. 1 must in some way suppress the LO-dependence during eddy current testing. If the transducer arrangement is inclined, the LO will vary from transducer to transducer so that unit 4 will largely interpret it as if one transducer moves across the test object with a varying LO-distance. The invention therefore advantageously comprises the principles described in the above-mentioned patents/applications and the terminology and contents of which are otherwise applicable to this specification.

In light of the above, the invention can broadly be described as a device based on a transducer multiplex method in combination with a vector transformation technique, or perhaps, more simply, as a vector transformation in combination with a simulated transducer movement based on the use of a plurality of transducers.

The invention also comprises compensation for the influence of the lift-off variation as described in British Patent 2041535, but in that case, as well as in the case of vector transformation, for example together with one imaginary/simulated transducer and transducer movement. The compensation which, by means of a control servo, aims at balancing signals emanating from a transducer to zero, operates in the present invention, for example via a multiplex method, with several transducers in a certain sequence, for example such that the respective transducer during its time portion is completely or partially compensated. In this way, also the compensation part may be common to all transducers, which, of course, is an advantage.

Both vector transformation techniques and compensation techniques are known, per se, from the above-mentioned patents/applications. However, using these techniques for transformation and compensation in association with an imaginary or simulated transducer is unique and is not—as far as is known—described in the specialist literature. A consequence of this is that the invention also embraces the use of several carrier frequencies and/or carrier frequency components.

Figure 5:
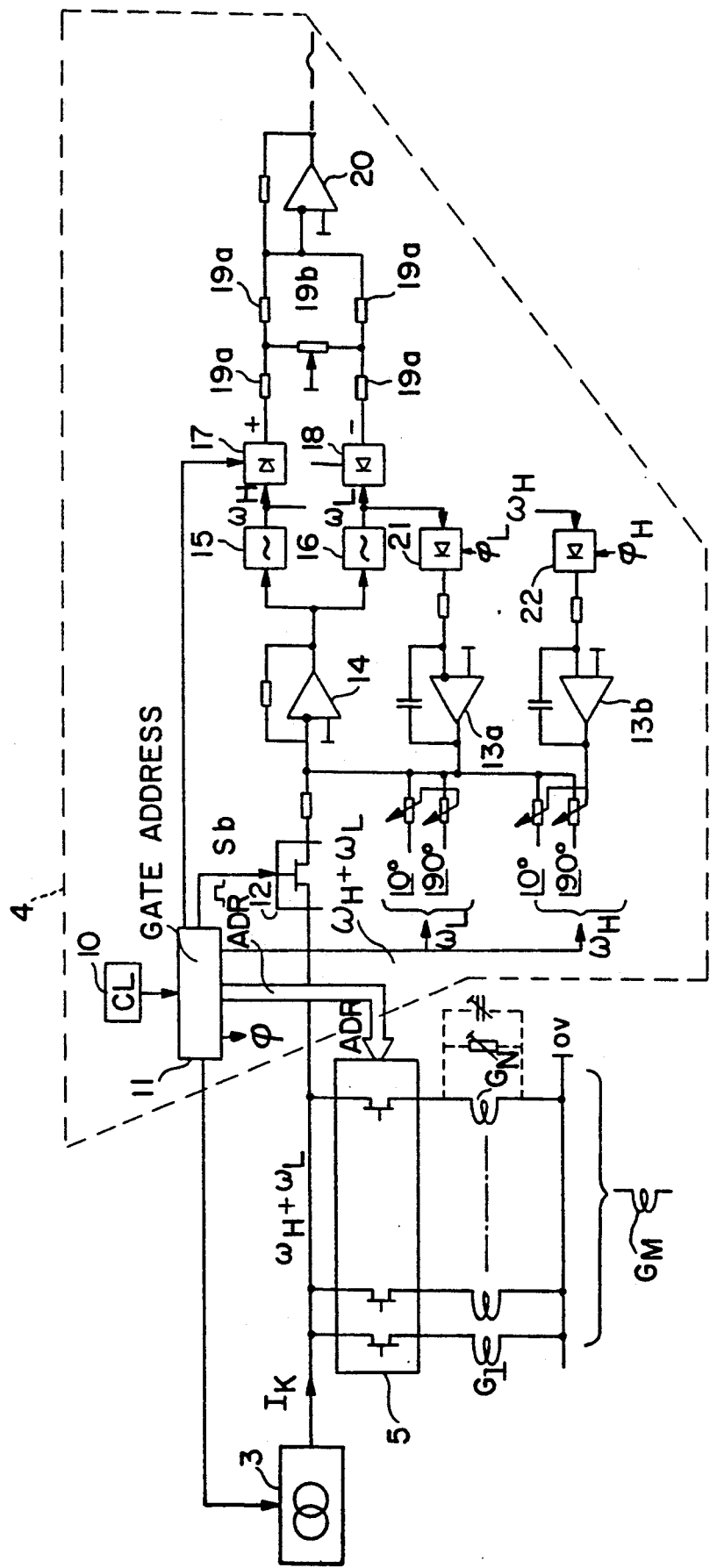
FIG. 5 is a circuit for use with the combination transducer arrangements showing means for balanced transducers.

As an example of how transducers can be individually balanced, trimming components are shown in dashed lines for the transducer $G_n$ in FIG. 5. Sometimes also trimming resistors may be positioned in series with the transducers, for example to compensate for a varying $R_{on}$ in the selector 5.

FIG. 5 shows a more detailed diagram of the layout and operation of a device according to the invention. Here a simulated transducer, representing several fixed transducers ($G_1$-$G_n$), has been shown as a movable transducer with the designation $G_M$. The subsequently arranged electronic components behave as if they are operating with the imaginary and movable transducer $G_M$, which is a characteristic feature of the invention. The transducer supply unit 3 feeds the transducer $G_M$ via the selector 5 which is switched by ADR signals from a unit 11 as will now be described.

In FIG. 5, the unit 10 consists of a clock oscillator (CL) which may advantageously be crystal-controlled. Gate Address 11, which is fed with clock pulses from the unit 10, comprises a counter, a decoder, a generator for gate pulses (Sb), transducer addresses (ADR), etc. Unit 12 is an analog gate which is opened by the Sb pulses. Unit 13a, 13b with associated electronic potentiometers, including phase-controlled rectifiers 21 and 22, constitute simple zero-compensation servos and should need no further explanation. Unit 14 consists of a simple operational amplifier. Units 15 and 16 define band pass filters tuned to the carrier frequencies in question, i.e. to a high frequency $\omega H$ and a low frequency $\omega L$, in the illustrated case. In this way, the different carrier frequencies are separated and have a different channel for each respective carrier frequency. Units 17 and 18 consist of phase-controlled rectifiers, the output signals of which are used as input signals to a transformation circuit, consisting of an array of resistors 19a and a balancing potentiometer 19b. The subsequent operational amplifier of summation type is shown at 20.

It should also be pointed out that the functions described in the invention can be realized by means of software as well as hardware. Using a computer or the like for storing digital measuring values, and so on, works quite excellently, and therefore this feature is also embraced by the invention.

The technique described in the aforementioned U.S. patent application Ser. No. 926,850 may be used with advantage within the scope of the signal processing part of the present invention; however, utilizing time delay of the imaginary and/or simulated transducer signal.

Figure 6:
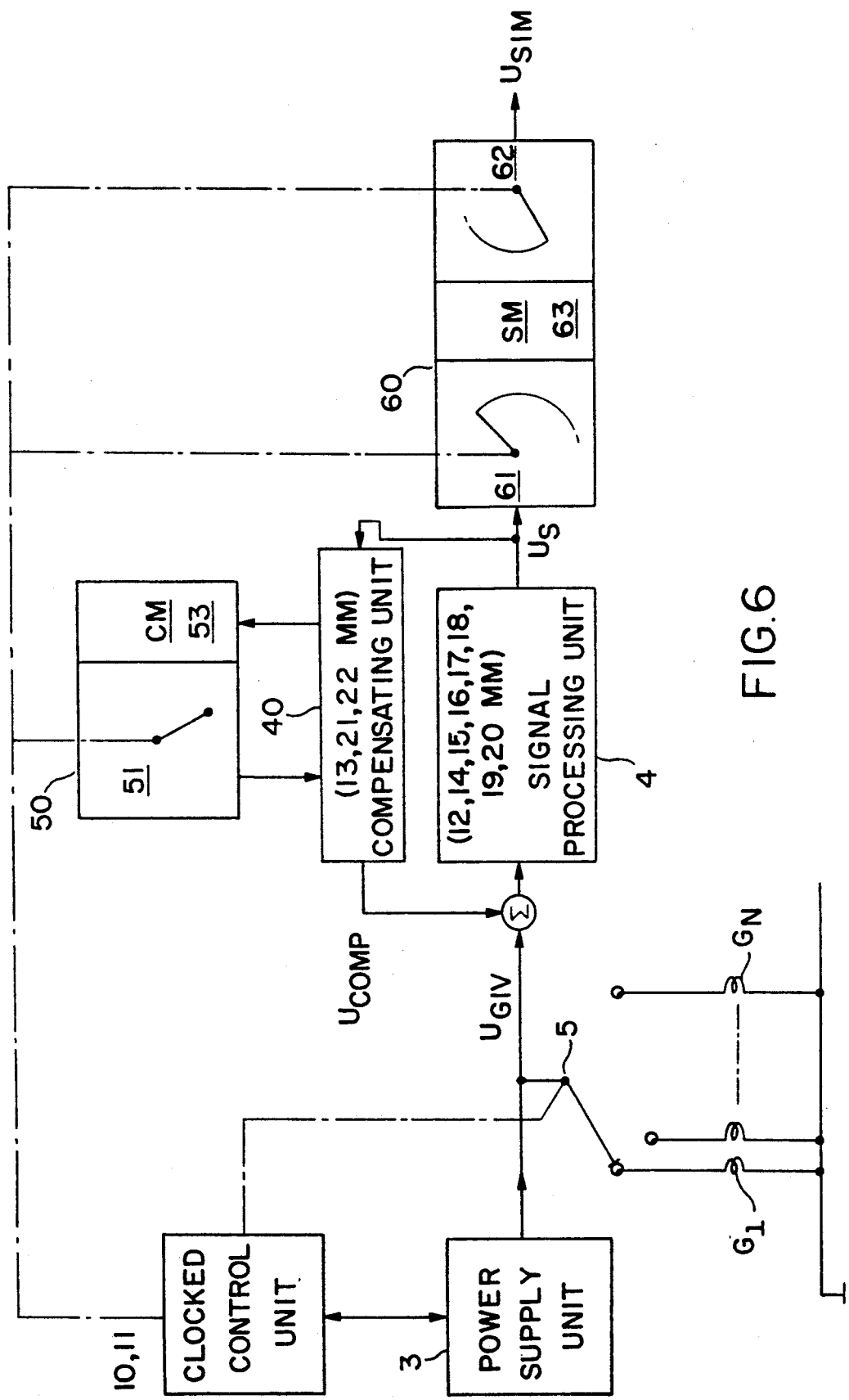
FIG. 6 shows a block diagram corresponding to FIG. 5.

FIG. 6 shows a block diagram corresponding to that shown in FIG. 5 but with the difference that a number of selector units are indicated at positions 51, 61 and 62, as well as at 5. Memory blocks are shown as units 53 and 63, 53 being a compensation memory (CM) and 63 a signal memory (SM). Unit 50 thus comprises the selector 51 and the compensation memory 53 and can be regarded as an important complement to a compensation unit 40. When the selector 5 steps from transducer to transducer in the composite transducer $G_M$, the selector 51 accompanies it at the same pace and in the same sequence and informs the compensation block 40 of the compensation requirement of each transducer $G_1$ ... $G_n$ in turn. The individual requirements are stored in the compensation memory 53. In this way, the unit 40 can rapidly assume the correct position for the transducer in question and thereby also rapidly generate the correct compensating voltage $U_{COMP}$. If the unit 50 were to be omitted, the unit 40 would not be able to compensate for differences between the respective transducers during the short time that each respective transducer is active. In other words, it would be necessary to use one compensating unit 40 per transducer, which for reasons which are easily understood would be disadvantageous, perhaps almost impossible, when the number of transducers is great, for example greater than fifty. With unit 50 it is possible to have one or at most a few compensation units 40, since the performance of the unit, especially as regards its speed of action in generating different compensating voltages $U_{COMP}$, is markedly increased as a consequence of the use of the unit 50. The memory unit 50 makes possible, for example, an instantaneous course adjustment of the unit 40 with the aid of information from the memory 53 when switching in the respective transducer.

Figure 8:
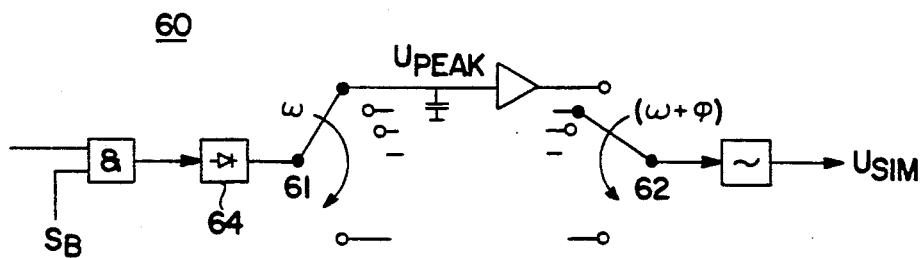
FIG. 8 is a detail of the circuit of FIG. 7.

FIG. 6 indicates how a signal ($U_S$) from the signal processing unit 4 is fed to a time-transforming unit 60. This unit includes the selector 61 which distributes the input signal $U_S$ to the signal memory (SM) 63. This memory may consist of a parallel condenser storage unit, for example as indicated in FIG. 8. If the selectors 5 and 61 are allowed to operate at the same velocity, for example synchronously, the signal from each transducer will be stored in its respective memory element, for example a capacitor. The memory is then updated once per sequence, i.e. each time that the selector 61 addresses the memory element in question. If then the memory is sensed with the selector 62, a signal $U_{SIM}$ can be generated, which simulates an imaginary, fictitious transducer. Because the memory also serves as an extender of gated signals, the signal $U_{SIM}$, after filtering, may be substantially free from switching disturbances, and the like.

It should also be noted that the selectors 61 and 62 need not run synchronously with each other. If the selector 62 steps at a different rate to the selector 61, a time transformation function is obtained which may, in certain respects, be most useful.

By varying the order of the connection of the memory elements to the selector 62, different surface scanning patterns for the simulated transducer $G_M$ can be generated in a simple manner, in other words, such that the transducer $G_M$ is conceived as if it moved in different paths across the surface of the test object.

Figure 7:
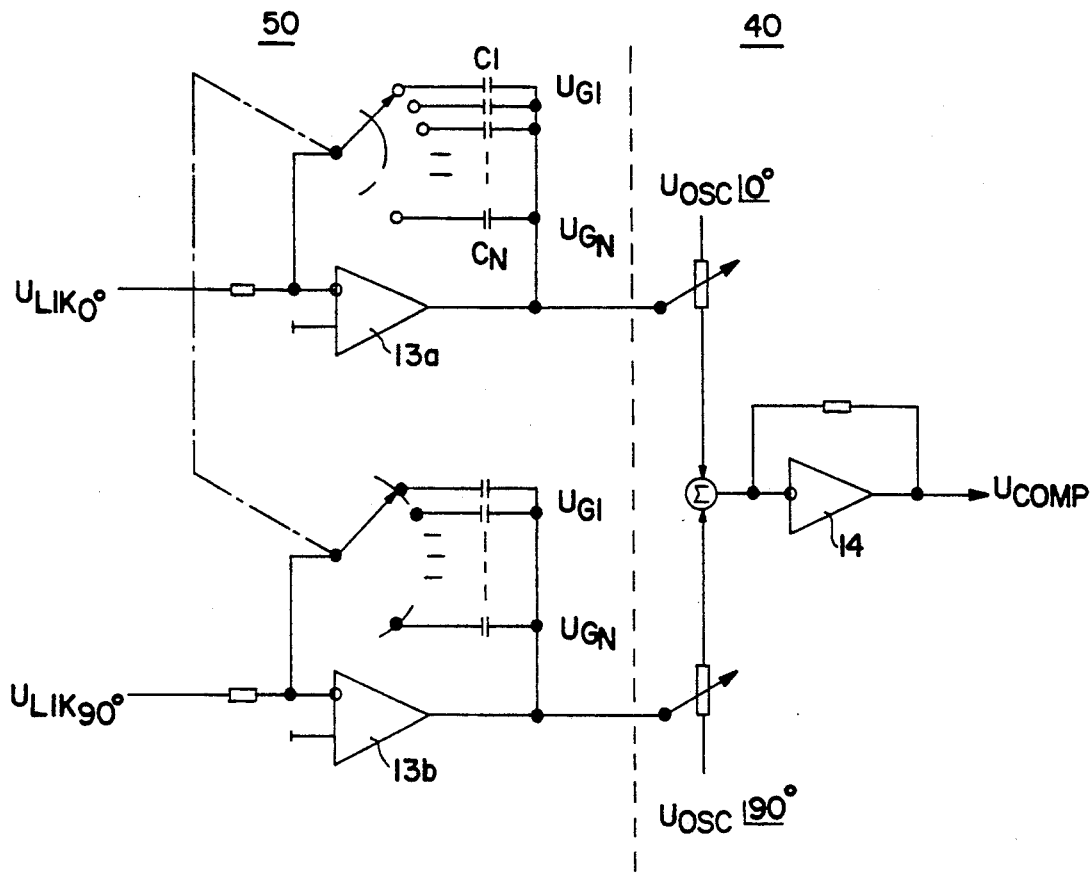
FIG. 7 shows examples of two integrators which can be used to provide a compensation function.

FIG. 7 shows one example of how integrators, included in the compensation control function, can be provided with a number of capacitors ($C_1-C_n$) which act as components of a simple compensation memory CM, storing information between the recurrent transducer switching sequences. The capacitors are selected and switched in such that each transducer has its own capacitor or capacitors. In this way, the output of the integrator will intermittently assume the correct compensating voltage for the respective transducer when this is switched in and will thereafter, in the usual way, operate during the time that the particular transducer is switched in. The integrators in FIG. 7 may also in themselves constitute memories, for example such that each transducer is allocated at least one integrator memory.

The integrators in FIG. 7 correspond to units 13a, 13b in FIG. 5, and as shown in FIG. 7 they can be used for generating separate compensation vectors, for example perpendicular to each other, and thereafter can be summed to obtain a resultant of the desired magnitude and direction which balances the transducer in question. This resultant compensation vector may contain several carrier frequencies, thus, for example, composed of several vectors, for example one for each carrier frequency in question. The compensation vector is designated $U_{COMP}$ in FIG. 7. As will be clear, it is adequate, in a simple case, to use capacitors as memory elements so that the compensation requirement of each respective transducer is temporarily represented by the appropriate capacitor voltage $U_{G1} \ldots U_{GN}$.

There is also a limit to the number of individual transducers that a compensation unit 40 is able to serve. In the case of a large number of transducers, for example one hundred, the unit 40 has 1/100th of the time within which to be able to update the memory 53 and to compensate the individual transducer in question, which places certain demands on the control unit. In such cases, it may be suitable to divide the composite transducer GM into groups of, for example thirty-two transducers per group, and to allot one compensation unit 40 to each such group, which then means that a smaller number of units 40 is used for a larger number of individual transducers.

If the test object moves relative to the transducer arrangement which, for example, is located in a plane above a billet surface, the distance between the transducer and the surface of the test object will probably have varied somewhat between each time that a certain transducer is switched in. The result of this is that the compensating voltage $U_{COMP}$ which is generated as a function of information in the compensation memory CM is not perfect, but a certain lift-off disturbance is obtained. This disturbance occurs on the signal $U_S$ in FIG. 6 and also occurs on the signal $U_{SIM}$. Since this lift-off (LO) disturbance for the most part also occurs in the signals from adjacently located transducers, which are, to a first approximation, at the same distance from the surface of the test object, the total effect of the LO disturbance will have the same character as if it originated from an imaginary, fictitious transducer $G_M$ which moves at a superimposed velocity determined by the rate of stepping of the selector 5. The consequence of this is that both $U_S$ and $U_{SIM}$ can be signal-processed using, for example, vector transformation techniques, for example via units 19 and 20 in FIG. 5, for example for suppressing LO-disturbances or other undesired influences on the signal.

As described in the literature, it is possible to choose among a number of transducers which are switched in differentially at a slow rate, i.e. a type of so-called position difference measurement, thus varying the field direction so that cracks having different orientation can be detected. However, this is something different from the successive transducer switchings described here which, in principle, bring about a relatively continuously movable field. The disadvantage of the known principles is, among other things, that they are too slow to be used when, for example, scanning test objects which move rapidly relative to the transducer arrangement and where the requirement for the minimum detectable crack length is considerable.

By making it possible, according to the present invention, to utilize the transducer signals in chosen sequences electronically and at a high rate by using the special compensation technique in combination with a gating process, completely new perspectives are opened up, where the mechanical complexity of the transducer arrangement can be drastically reduced.

Unit 60 in FIG. 6 is shown in more detail in FIG. 8. By gating the signal $U_S$ to a peak value rectifier 64, the memory cells will in this example be charged, via the selector 61, to a voltage $U_{PEAK}$, which then directly or indirectly represents the impedance variation of a chosen transducer, including the influence of a quantity, for example a surface crack. The selector 62, which is here intended to operate with a certain slip (W+Q) relative to the selector 61 (W), senses the capacitor voltages in question, one at a time, whereby the signal $U_{SIM}$ is generated after suitable filtering. One of the characteristics of the invention is that this signal, $U_{SIM}$, represents the output of an imaginary transducer $G_M$, and that the signal $U_{SIM}$ is signal-processed, for example via vector transformation techniques, as if it directly or indirectly originated from a real transducer which moves in a certain path relative to the test object or a surface thereof.

In practice, it is always possible to attempt to multiply all the functions, thus obtaining just as many measuring units as transducers. In those cases where it is desired to operate with a large number of transducers, for example more than fifty, it is immediately realized that the electronic measuring equipment will be very extensive. It is probably impossible in practice to cope with such a vast and extensive amount of electronics.

In the case of crack detection, the aim is often that the real or simulated transducer movement, for example the speed of rotation and path/surface scanning pattern of the transducers, should form such a fine-meshed scanning pattern on the surface of the test object that the demands on the minimum detectable crack length are fulfilled irrespective of the orientation of the crack on the test object, taking into consideration the relative movement of the test object with respect to the transducer arrangement. By applying the teachings of FIGS. 5 and 6, including combinations and variations thereof, the above-mentioned aim can be realized in the majority of conceivable applications without the electronics becoming too extensive or difficult to cope with.

Imperfections in the shape, position, etc., of the respective transducer, both with respect to the test object and between the transducers themselves, cause the simulated transducer ($G_M$) or transducer signal if uncompensated, to occur as a greatly disturbed, for example "jumping" transducer. The method of compensation described in the present invention is a dynamic compensation individually adapted to the respective transducer, which makes possible a very rapid compensation of the respective transducer, whereby the above-mentioned disturbance can be greatly reduced.

Since the number of transducers that may be served per electronic measuring unit is limited, it may be suitable to allow the arrangement according to FIG. 4 to move across the direction of movement of the test object. The same is true with the arrangement according to FIG. 3.

A long-felt wish is to be able to operate with a stationary transducer arrangement, which is possible according to the present invention. A requirement for this, however, is that the transducer can scan the test object in such a way that no cracks may pass the transducer arrangement without being detected i.e. that the field configurations of the transducers are largely homogeneous. This is achieved by the scanning regions of the individual transducers coinciding with, or even better, overlapping each other. Any overlap should be of such an extent that a short crack, despite its orientation, is always capable of disturbing the eddy current field configuration to approximately the same extent irrespective of the position of the crack on the surface of the test object.

In the case of low velocities of the test object, the requirements for field overlapping may be reduced if the transducer arrangement is oscillated, for example transverse to the direction of movement of the test object. The oscillation amplitude is then suitably adapted to the mutual distances of the transducers, so that the oscillation amplitude can be minimized.

An effect which may be worth noting is that if, for example, a very long crack is located below one and the same transducer for a long period of time, the dynamic compensation will have compensated away the crack signal after some time, which in certain cases, especially in connection with rolled wire testing, may be disadvantageous. This may be a further reason for oscillating the transducer arrangement with a limited amplitude and frequency. A suitable oscillation amplitude may be ±10–20 mm and a suitable oscillation frequency may be 1–5 Hz.

Now, if it is desired to avoid the oscillation completely, a very interesting complement may be resorted to, which, however, is somewhat more complicated. This complement is based on the "absolute" measurement being combined with a successive "difference" measurement. Since a number of symmetrically arranged transducers are available, the conditions are almost ideal for measuring also differentially between adjacent transducers and, for example, scanning the transducers in FIG. 3 in pairs (e.g. such as with $G_1$-$G_2$, $G_2$-$G_3$, $G_3$-$G_4$, and so on) in a continuous succession. In this way, it will also be possible to detect, in principle, infinite cracks. Also in this case, of course, the measured values may be stored away and the results from different sequences can be compared with each other in order to sophisticate the measuring method still further.

The invention can be varied and applied in many ways within the scope of the appended claims and acccompanying drawings.

What is claimed is:

1. A device for monitoring a test object with respect to at least one detectable characteristic thereof, such as a crack, said device comprising:

a plurality of eddy current type transducers mounted so that each transducer monitors at least partially different adjacent regions of said test object to scan over a wider test object than covered by each region;

power supply means for energizing said plurality of transducers to generate respective output signals;

signal processsing means for processing and combining said output signals to provide a resultant output signal representing said at least one detectable characteristic from the monitoring of desired regions of said test object;

means for vector transformation of said resultant output signal to provide a vector transformed resultant output signal;

selector means for selectively sequentially feeding said respective output signals from each of said plurality of transducers to said signal processing means, to obtain said monitoring of desired regions of said test object;

a plurality of updatable memories for storing respective compensation data for each of said plurality of transducers;

means for compensating said respective output signals; and memory selector means for selectively retrieving said respective compensation data from said plurality of updatable memories and selectively feeding said compensation data to said means for compensating.

2. A device according to claim 1, in which the position of said plurality of transducers relative to one another and the test object is adjustable in at least one dimension.

3. A device according to claim 1 in which each transducer of said plurality of transducers at least partially consists of a coil of metallic foil.

4. A device according to claim 3, in which said plurality of transducers are formed on at least one side of a flexible laminated sheet by etching.

5. A device according to claim 4, further comprising means on the laminated sheet for modifying the properties of each transducer to balance the impedance thereof.

6. A device according to claim 1, in which said power supply means energizes said plurality of transducers during respective consecutive time periods and said selector means includes gating means for gating the output signal of each transducer during only a central part of said time period of the output signal in question to eliminate noise.

7. A device according to claim 1, in which said selector means includes means for storing vector transformed resultant output signals obtained at different times and means for comparing a vector transformed resultant output signal obtained at one time with a vector transformed resultant output signal obtained at another time.

8. A device according to claim 1, in which said power supply means is a constant current generator common to at least the majority of said plurality of transducers.

9. A device according to claim 1, in which said plurality of transducers is mounted on a common support and further comprising means for oscillating said support.

10. A device according to claim 1, further comprising means for generating at least one signal as a function of output signals from different transducers such that said signal can be regarded as being obtained from said imaginary movable transducer, and wherein said signal processing means includes means for signal processing said at least one signal starting from the properties of said imaginary transducer.

11. A device according to claim 1, further comprising means for at least partially suppressing at least one effect caused by a varying parameter, for example the distance (LO) between each transducer and the test object, by processing said respective output signals using vector transformation utilizing different carrier frequencies.

12. A device according to claim 1, further comprising a support for supporting said individual transducers to sense areas of the surface of the test object which largely coincide with one another.

13. A device according to claim 1, wherein said means for processing further comprising signal transforming means for suppressing at least one effect in said output signals caused by a varying parameter of said plurality of transducers.

14. A device according to claim 13, wherein said at least one effect is the distance between each one of said plurality of transducers and the surface of the test object.

15. A device according to claim 1, wherein said power supply means, means for compensating and said signal processing means each operate with the same two different carrier frequencies.

16. A device according to claim 1, wherein said test object is rolled wire and said plurality of transducers are evenly positioned around the periphery of said rolled wire.

17. A device according to claim 16, in which said plurality of transducers are arranged in a zigzag pattern.

18. A device for monitoring a test object with respect to at least one detectable characteristic thereof, such as a crack, said device comprising:
- a plurality of eddy current type transducers mounted so that each transducer monitors at least partially different adjacent regions of said test object to scan over a wider test object than covered by each region;
- power supply means for energizing said plurality of transducers to generate respective output signals;
- signal processing means for processing said output signals by means of vector transformation and combining the vector transformed signals to provide a vector transformed resultant output signal representing said at least one detectable characteristic from the monitoring of desired regions of said test object;
- selector means for selectively sequentially feeding said respective output signals from each of said plurality of transducers to said signal processing means, to obtain said monitoring of desired regions of said test object;
- a plurality of updatable memories for storing respective compensation data for each of said plurality of transducers;
- means for compensating said respective output signals; and
- memory selector means for selectively retrieving said respective compensation data from said plurality of updatable memories and selectively feeding said compensation data to said means for compensating.

19. A device according to claim 18 further comprising means for vector transformation of said output signals to provide vector transformed signals and said signal processing means also combines said vector transformed output signals.

20. A device according to claim 19, further comprising means for at least partially suppressing at least one effect caused by a varying parameter by processing said respective output signals using vector transformation utilizing different carrier frequencies.

* * * * *